US009775502B2

(12) United States Patent
Miller et al.

(10) Patent No.: US 9,775,502 B2
(45) Date of Patent: Oct. 3, 2017

(54) LAPARASCOPE AND ENDOSCOPE CLEANING AND DEFOGGING DEVICE

(71) Applicant: Buffalo Filter LLC, Lancaster, NY (US)

(72) Inventors: Michael J. Miller, Depew, NY (US); William J. Kellner, Amherst, NY (US); Anthony L. Lizauckas, III, Williamsville, NY (US); Gregory Pepe, Lancaster, NY (US); Samantha Bonano, Williamsville, NY (US)

(73) Assignee: Buffalo Filter LLC, Lancaster, NY (US)

( * ) Notice: Subject to any disclaimer, the term of this patent is extended or adjusted under 35 U.S.C. 154(b) by 189 days.

(21) Appl. No.: 14/779,986

(22) PCT Filed: May 6, 2015

(86) PCT No.: PCT/US2015/029479
§ 371 (c)(1),
(2) Date: Sep. 25, 2015

(87) PCT Pub. No.: WO2015/171771
PCT Pub. Date: Nov. 12, 2015

(65) Prior Publication Data
US 2016/0135673 A1 May 19, 2016

Related U.S. Application Data

(60) Provisional application No. 61/989,220, filed on May 6, 2014.

(51) Int. Cl.
*A61B 1/12* (2006.01)
*A61B 1/00* (2006.01)
(Continued)

(52) U.S. Cl.
CPC .......... *A61B 1/123* (2013.01); *A61B 1/00131* (2013.01); *A61B 1/126* (2013.01);
(Continued)

(58) Field of Classification Search
CPC ...................................... A61B 1/123
See application file for complete search history.

(56) References Cited

U.S. PATENT DOCUMENTS 3,980,078 A 9/1976 Tominaga
4,279,246 A 7/1981 Chikama
(Continued)

FOREIGN PATENT DOCUMENTS

WO 2004080294 A1 9/2004
WO 2012169433 A1 12/2012
WO 2013012790 A2 1/2013

*Primary Examiner* — Jason Ko
(74) *Attorney, Agent, or Firm* — Michael J. Berchou, Esq.; Timothy W. Menasco, Esq.; Harter Secrest & Emery LLP (57) ABSTRACT

A laparascope and endoscope cleaning and defogging device with a port located horizontally that is used to warm the scope prior to insertion into the body cavity/surgical site. The scope punctures the initial membrane and enters the cavity between two bodies of absorbent material that contain fluid. The absorbent material is arranged such that the passage of a scope would be accommodated for different sizes of surgical scopes. A circuit board is located on the bottom of the chamber that has a design element used to warm the liquid to a temperature equal to or greater than the temperature of the proposed surgical environment. When the scope is located between the two absorbent bodies, the heat generated by the circuit board is transferred via the liquid and contacts the scope, warming it in preparation for surgery.

25 Claims, 12 Drawing Sheets

(51) Int. Cl.
  *B08B 1/00* (2006.01)
  *B08B 3/10* (2006.01)
  *A61M 25/00* (2006.01)

(52) U.S. Cl.
  CPC .............. *A61B 1/127* (2013.01); *A61B 1/128* (2013.01); *B08B 1/001* (2013.01); *B08B 3/10* (2013.01); *A61M 2025/0019* (2013.01)

(56) References Cited

U.S. PATENT DOCUMENTS

| | | |
|---|---|---|
| 4,805,598 A | 2/1989 | Ueda |
| 5,225,001 A | 7/1993 | Manni et al. |
| 5,237,984 A | 8/1993 | Williams, III et al. |
| 5,274,874 A | 1/1994 | Cercone et al. |
| 5,313,934 A | 5/1994 | Wiita et al. |
| 5,339,800 A | 8/1994 | Wiita et al. |
| 5,347,988 A | 9/1994 | Hori |
| 5,351,675 A | 10/1994 | Brodsky |
| 5,382,297 A | 1/1995 | Valentine et al. |
| 5,386,817 A | 2/1995 | Jones |
| 5,392,766 A | 2/1995 | Masterson et al. |
| 5,400,767 A | 3/1995 | Murdoch |
| 5,413,092 A | 5/1995 | Williams, III et al. |
| 5,448,990 A | 9/1995 | De Faria-Correa |
| 5,458,633 A | 10/1995 | Bailey |
| 5,464,008 A | 11/1995 | Kim |
| 5,518,502 A | 5/1996 | Kaplan et al. |
| 5,533,496 A | 7/1996 | De Faria-Correa et al. |
| 5,549,543 A | 8/1996 | Kim |
| 5,605,532 A | 2/1997 | Schermerhorn |
| 5,647,840 A | 7/1997 | D'Amelio et al. |
| 5,651,757 A | 7/1997 | Meckstroth |
| 5,894,369 A | 4/1999 | Akiba et al. |
| 5,910,106 A | 6/1999 | Morgan |
| 6,017,333 A | 1/2000 | Bailey |
| 6,231,596 B1 | 5/2001 | Collins |
| 6,234,635 B1 | 5/2001 | Seitzinger et al. |
| 6,712,479 B1 | 3/2004 | Seitzinger et al. |
| 7,080,641 B2 | 7/2006 | Gomez |
| 7,291,308 B2 | 11/2007 | Wu et al. |
| 7,311,660 B2 | 12/2007 | Gomez |
| 7,537,563 B2 | 5/2009 | Temple |
| 7,648,023 B2 | 1/2010 | Maguire, Jr. et al. |
| 7,671,302 B1 | 3/2010 | Faries, Jr. et al. |
| 7,727,262 B2 | 6/2010 | Shaolian et al. |
| 7,803,109 B2 | 9/2010 | Gomez |
| 8,001,984 B2 | 8/2011 | Sasaki |
| 8,047,215 B1 | 11/2011 | Sasaki |
| 8,148,667 B2 | 4/2012 | Faries, Jr. et al. |
| 8,152,717 B2 | 4/2012 | Gomez |
| 8,153,937 B2 | 4/2012 | Faries et al. |
| 8,185,997 B2 | 5/2012 | Heck |
| 8,376,936 B2 | 2/2013 | Wu et al. |
| 8,400,499 B2 | 3/2013 | Kogane |
| 8,480,699 B2 | 7/2013 | Ihde, II |
| 8,550,988 B2 | 10/2013 | Pribanic |
| 2002/0022762 A1 | 2/2002 | Beane et al. |
| 2008/0194915 A1 | 8/2008 | Blackhurst et al. |
| 2009/0112057 A1 | 4/2009 | Kammer et al. |
| 2009/0247832 A1 | 10/2009 | Temple |
| 2010/0270295 A1 | 10/2010 | Wang |
| 2012/0187104 A1 | 7/2012 | Heymann et al. |
| 2012/0197084 A1 | 8/2012 | Drach et al. |
| 2012/0238818 A1 | 9/2012 | O'Prey et al. |
| 2013/0186428 A1 | 7/2013 | Lutz et al. |
| 2015/0080660 A1 | 3/2015 | Gomez et al. |

LAPARASCOPE AND ENDOSCOPE CLEANING AND DEFOGGING DEVICE

CROSS-REFERENCE TO RELATED APPLICATION

The present invention claims priority benefit of U.S. Provisional Patent Application No. 61/989,220 filed May 6, 2014 and entitled "Laparascope and Endoscope Cleaning and Defogging Device," which is hereby incorporated by reference.

TECHNICAL FIELD

The present invention relates generally to laparoscopic and endoscopic surgery, and more specifically, to a device that warms, cleans, and defogs the laparoscope or endoscope before and during medical procedures that utilize that technology for visualization.

BACKGROUND

A laparoscope or endoscope is used in conjunction with a camera system for visualization during surgical procedures. When the scope is introduced from ambient room temperature into a cavity at body temperature, the rapid change causes the lens to fog. During surgery, the introduction of surgical tools such as an electrosurgical device deliver energy, creating heat, and vaporizes the intracellular fluid, which increases the pressure inside the cell and eventually causes the cell membrane to burst. When this happens, a plume of smoke containing mostly water vapor is created, along with the aeration of cellular debris. During procedures involving a scope, many times this water vapor, smoke plume, and/or cellular debris attach to the lens, impairing the view of the surgical site.

BRIEF SUMMARY

The new apparatus and system described and illustrated herein is designed to improve and/or maximize the visualization of the scope during surgical procedures.

In one aspect, the device has a port located horizontally that is used to warm the scope prior to insertion into the body cavity/surgical site. The scope enters the cavity between two bodies of absorbent material that may or may not contain fluid. The absorbent material is arranged such that the passage of a scope would be accommodated for a size range of 1 mm up to 15 mm in diameter. A circuit board is located on the bottom of the chamber that has a design element used to warm the liquid to a temperature sufficient to reduce or eliminate issues related to temperature differences between the surrounding environment and the body of the patient. When the scope is located between the two absorbent bodies, the heat generated by the circuit board is transferred to the scope, warming it in preparation for surgery. Also within this chamber is a V-shaped member of white, non-porous material that may be used to white balance the camera. The V-shape allows for multiple different sizes of scopes ranging from 1 mm to 15 mm to accurately white balance per the camera system procedure.

In another aspect, a separate stand or cradle is supplied with the device to hold the scope during the warming procedure. When the scope is aligned horizontally, there is a chance that the scope and camera could dislodge from the device and become damaged due to a fall or shock. The stand is designed and supplied with the main device to cradle the scope and camera while in the horizontal position, limiting the possibility of damage from fall or shock.

The circuit board and electronics of the device are designed such that multiple and separate heater sections are built into the circuit (either flex or rigid construction). The electronic control circuit is designed to maintain temperature of the heating circuit for a period of time for warming the fluid. The heating element is designed with enough resistance to achieve the desired heating performance, and protect against thermal runaway in a single or multiple fault condition. The power supplied to the circuit board can be from a battery or batteries or alternately from a plug-in DC power supply. The battery power supply could be designed in such a way as to be removed separately for waste disposal separately from the main housing. The device would be activated by removing a non-conductive sheet located between the battery contacts, by actuating a switch, or by depressing a button.

In another aspect, the device has a port located vertically that is used to clean and warm the scope after use in the surgical site. The scope punctures the initial membrane and enters the cavity comprised of a cleaning surface and liquid that has been warmed by the circuit board. The cleaning surface may be comprised of a porous material such as a sponge or non-woven material or it could be comprised of a silicone or similar flexible material in a unique pattern or design for cleaning of the lens. The cleaning surface, along with a warm fluid located in the chamber is used to remove debris and/or fog that has accumulated on the lens during surgery that limits visualization for the user.

In another aspect, light emitting diodes are included in the device to illuminate both or either of the ports for identification. The LED(s) would illuminate once the heating element has been activated, confirming to the user the device was in-use. Also, during use the illumination of the port or ports would aid the user in identification of the device, especially in operation within a dimly lit room, typical of laparoscopic procedures.

DETAILED DESCRIPTION

Figure 1:
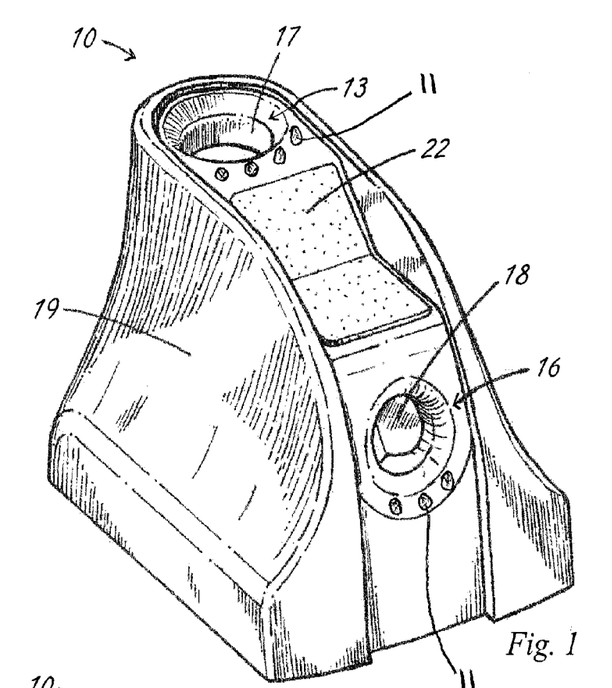
FIG. 1 is a perspective view of the main body of a scope cleaning device.

Turning to FIG. 1, the scope cleaning device 10 has a first opening 13 for receiving a generally vertically oriented scope and a second opening 16 for receiving a generally horizontally oriented scope. A plurality of illumination devices such as light emitting diodes 11 may be disposed around the openings 13, 16 to facilitate the insertion of the surgical scopes in darker environments. The openings 13, 16 may be sealed by a frangible disc 17, 18 made of an elastomeric material or the like. The seals are provided to seal the cleaning solution in the device prior to use. The scope cleaning device has a housing 19 that is closed and sealed to protect the internal compartments from exposure to outside elements. A microfiber wipe 22 may be mounted to the exterior of the housing 19 such that a scope 115 (FIG. 13) may be brought into contact with the wipe 22 to remove debris. The device 10 uses separate compartments to clean, warm and white balance a scope.

Figure 2:
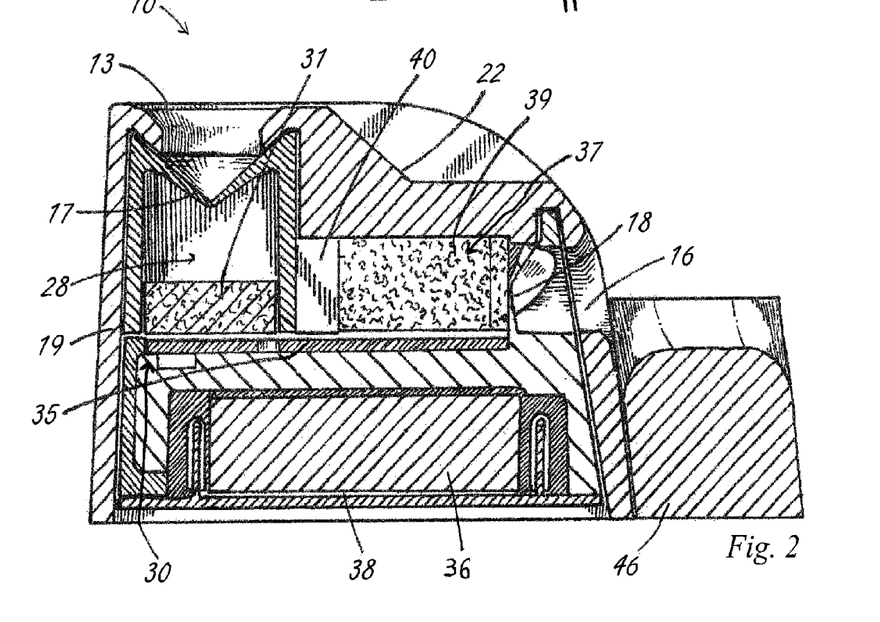
FIG. 2 is a cross-sectional view of the scope cleaning device of FIG. 1 with a stand added.
Figure 10:
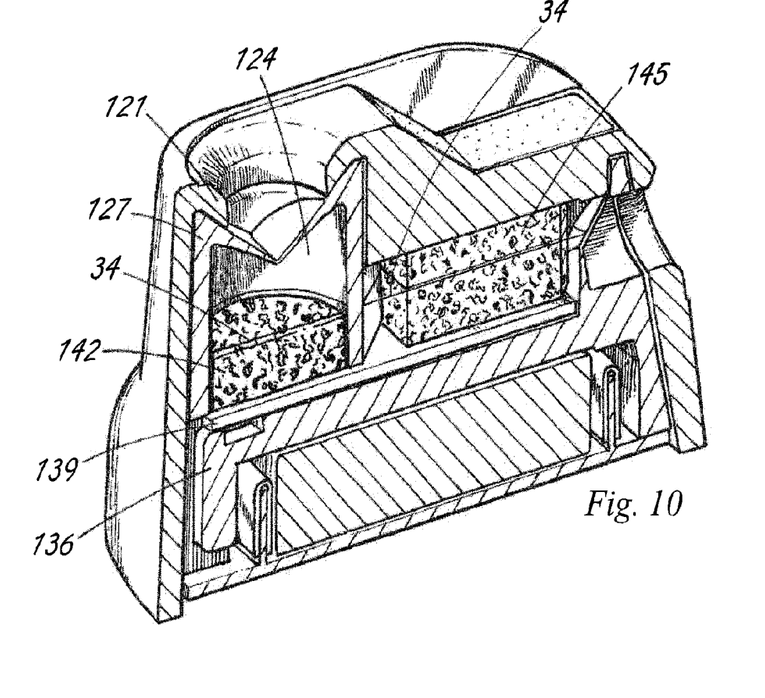
FIG. 10 is a detailed cross sectional view of a portion of the scope cleaning device of FIG. 6.

Turning to FIG. 2, the first opening 13 leads downward to the seal 17. A cavity 28 formed in the body of the housing receives the scope 115. A cleaning material 31 is positioned at the bottom of the cavity 28. The cleaning material 31 may comprise a sponge or other soft, porous material for receiving and holding a cleaning solution 34 (FIG. 10). The cleaning material 31 soaks up the liquid and transfers heat to the scope 115. The cleaning solution may be any biocompatible, sterile solution capable of being retained by the cleaning material 31 in the cavity 28. The end of the scope 115 is cleaned and warmed by contact with the cleaning material which may be partially immersed in the heated, cleaning solution 34. A resistance type electrical heating circuit 30 may be located underneath the cleaning material 31. The heating circuit 30 may include resistors on a printed circuit board 35. The electrical circuit 30 for generating heat through the resistors may be powered by a battery 36, battery pack, DC or AC power from an outlet. A battery compartment 38 may be located underneath the circuit board 35.

On the right hand side of the figure, second opening 16 extends to a second horizontally disposed cavity 37 for receiving the scope 115. The horizontally disposed cavity 37 may contain a pair of sponges or a cleaning material 39 that is split to provide a channel for sliding the scope 115 through the cleaning material 39. The two sponges are configured to accept and to warm scopes 115 of all sizes. A V-shaped white reference material 40 is disposed at the end of the cavity 37. The white balance reference material 40 is constructed of a non-porous material such as a silicone. The white balance reference material 40 does not hold any liquid or cleaning solution and is arranged to provide a white balance for providing a reference color for optimizing the camera. The white balance reference material 40 is V-shaped so that scopes 115 of different diameters may be inserted through the cleaning material 39 and into contact with the white balance reference material 40.

Figure 5:
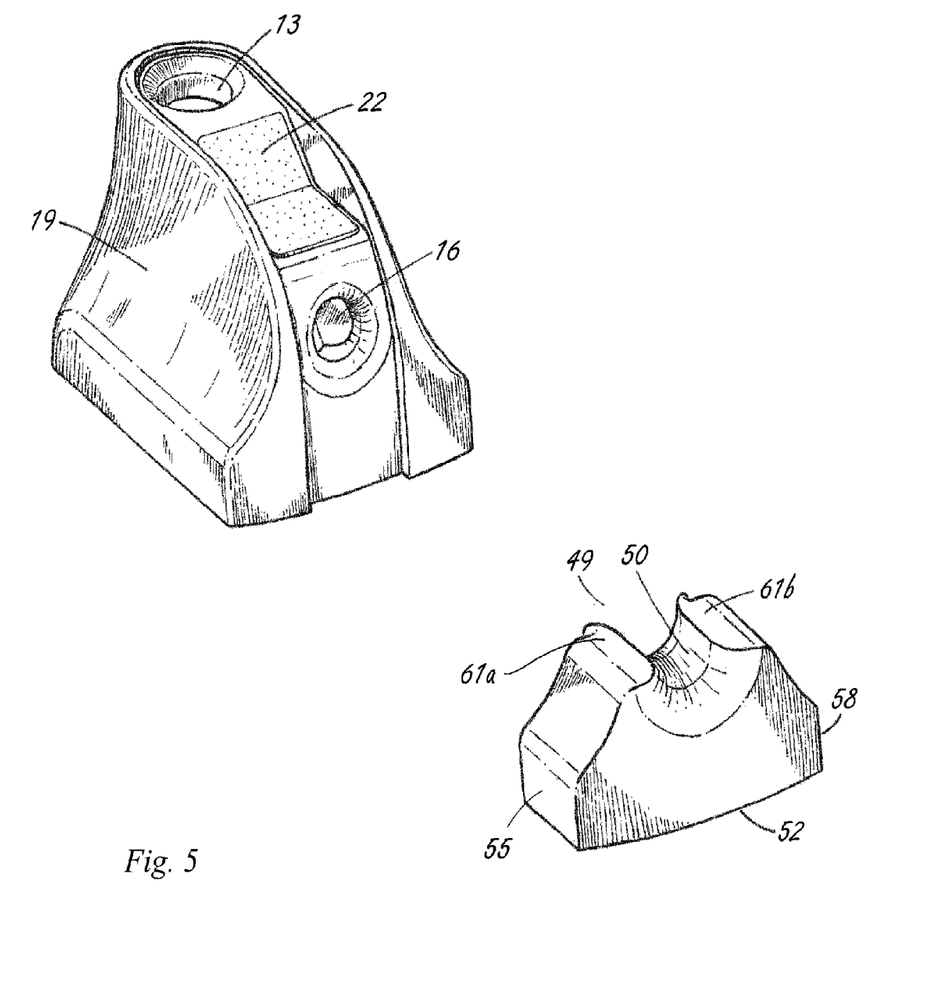
FIG. 5 is a perspective view of the main body and stand separated to highlight the ability to cradle a scope when arranged in the horizontal position.
Figure 13:
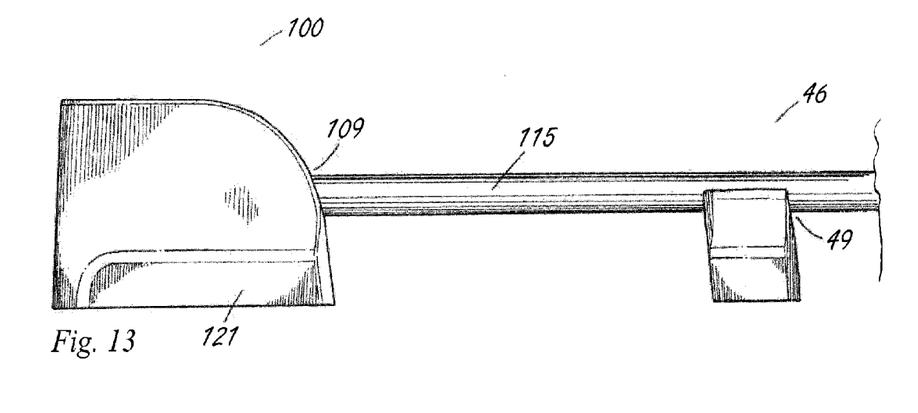
FIG. 13 is a side elevational view of the scope cleaning device and a stand for supporting a scope.

A stand 46 is shown in a position abutting with the housing 19. The stand 46 may also be disposed in spaced apart relation as shown in FIGS. 5 and 13. The stand 46 provides support for the scope 115 while it is inserted into the horizontally oriented cavity 37.

Figure 3:
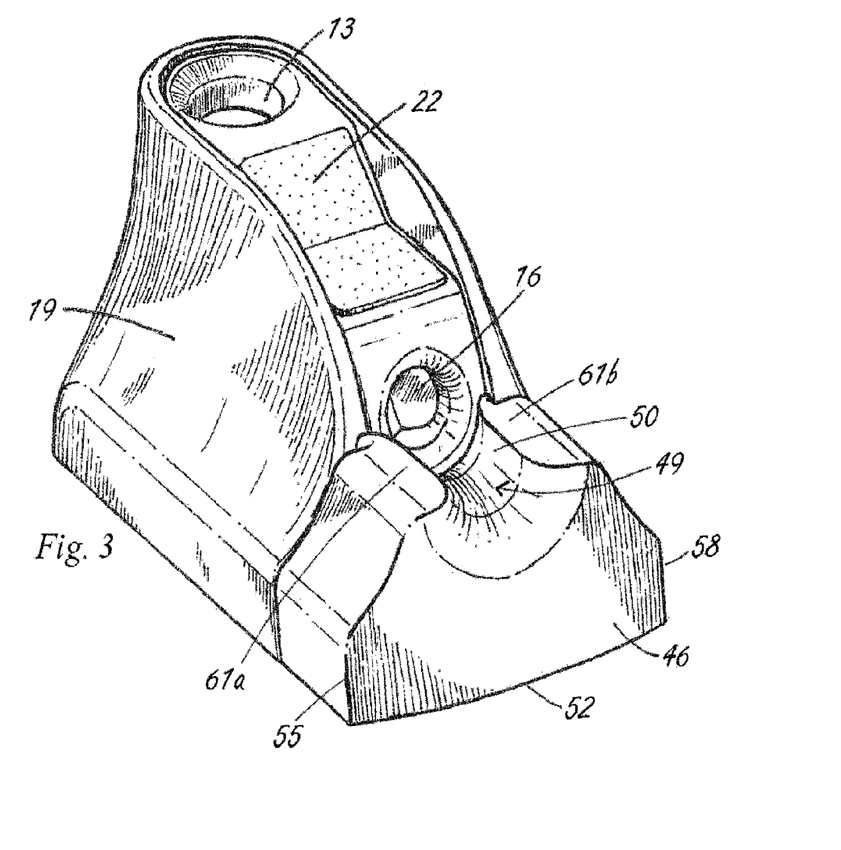
FIG. 3 is a perspective view of the main body and stand of a scope cleaning device.
Figure 4:
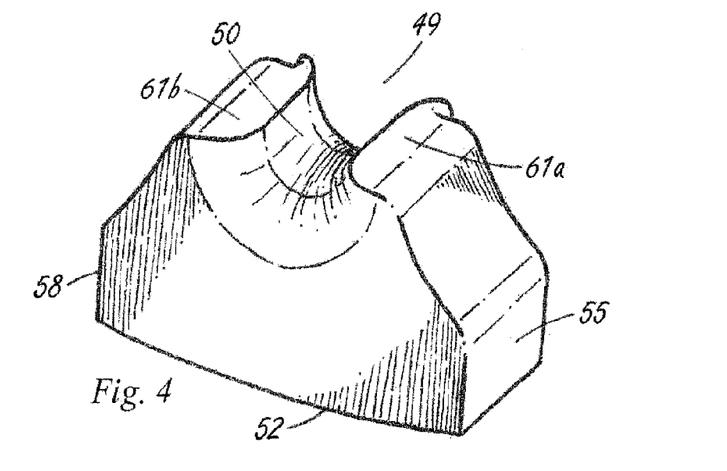
FIG. 4 is a perspective view of the stand of a scope cleaning device.

Turning to FIGS. 3 and 4, the stand 46 may be provided with an opening 49 bordered by a curved upper surface 50. The stand 46 may have a flat base 52 and a pair of side walls 55, 58. The side walls 55, 58 extend to a top surface 61a, 61b that borders the opening 49. The opening 49 is sized to be larger than the outside diameter of the scope 115 such that the scope 115 may slide into and out of the opening 49.

In FIG. 5, the stand 46 is disposed in spaced apart relation relative to the scope cleaning device 10. The stand 46 is disposed such that a scope 115 deployed in opening 16 will align with the opening 49 at the top of the stand 46.

Figures 6, 7:
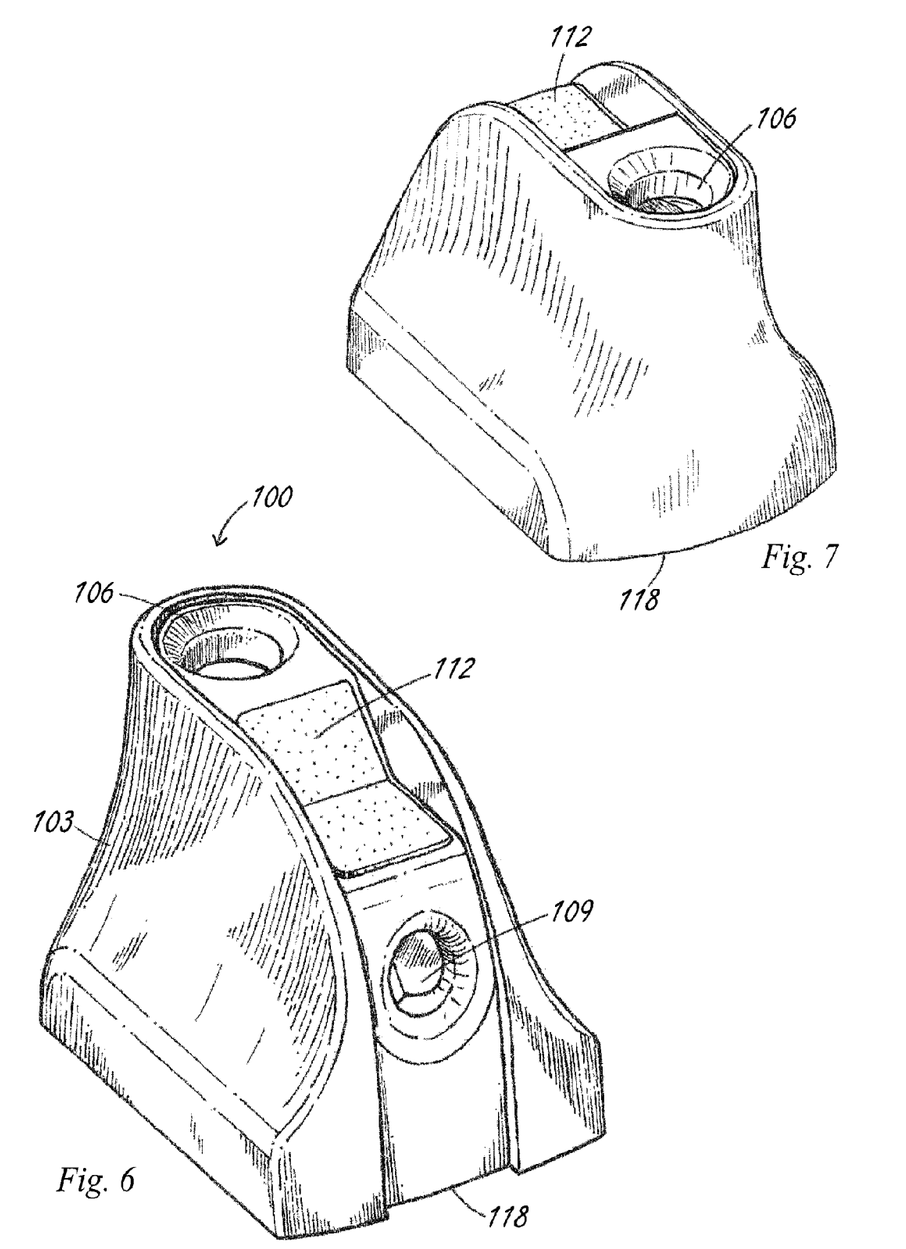
FIG. 6 is a perspective view of an alternate embodiment of the scope cleaning device.
FIG. 7 is a rear perspective view of the scope cleaning device of FIG. 6.

In FIGS. 6 and 7, scope cleaning device 100 is an alternate embodiment of scope cleaning device 10. The device 100 includes a housing 103 having a first opening 106 and a second opening 109. A microfiber wipe 112 may be disposed at the top of the housing 103 for manually wiping off a scope 115. As shown, the housing 103 may extend outward in both directions toward the base 118 of the device 110. The wider portion of the housing 103 at the base 118 provides for greater stability when inserting the scope 115.

Figure 8:
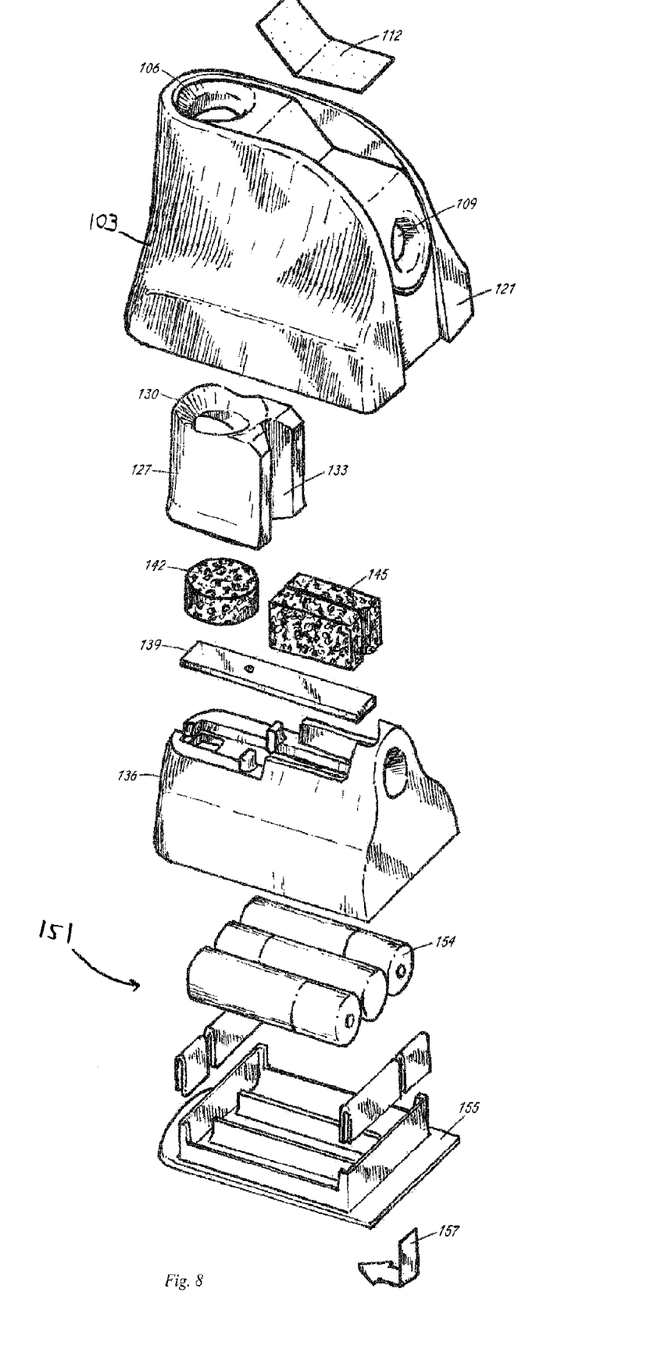
FIG. 8 is an exploded view of the scope cleaning device of FIG. 6.
Figure 9:
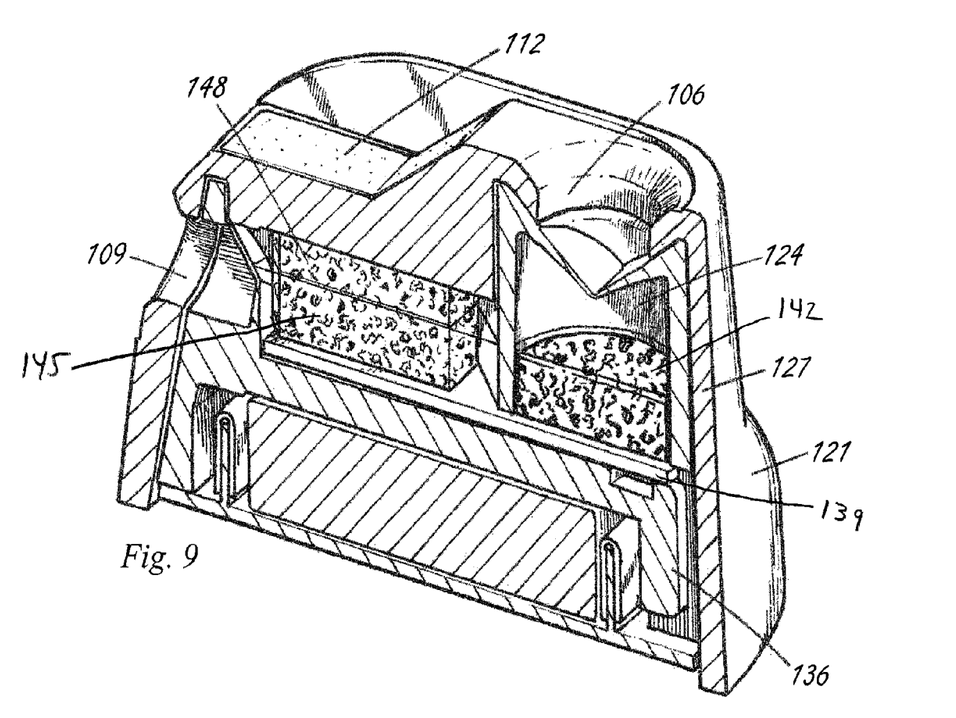
FIG. 9 is a cross-sectional view of the scope cleaning device of FIG. 6.

As shown in FIGS. 8 and 9, the device 100 includes the microfiber wipe 112 at the top of the housing 103. The housing 103 is a formed from a hollow shell 121 that forms internal cavities and protects the interior components from exposure to external elements. The first opening 106 may extend to a first chamber 124 (FIG. 9) formed in a subhousing 127. The subhousing 127 has an opening 130 at the top that provides a seal. The exterior of subhousing 127 may be formed on the right hand side with a V-shaped section that receives a white balance reference material 133. The subhousing 127 may be received on top of subhousing 136 that forms a base for supporting subhousing 127, printed circuit board 139, a first cleaning material 142 such as a sponge or the like disposed in subhousing 127, and a second cleaning material 145 that is disposed in a horizontal chamber 148 (FIG. 9). The second cleaning material 145 may comprise a pair of sponges 145a and 145b (best shown in FIG. 12) or cloths or may comprise a split cleaning material having a channel formed therein for receiving the scope 115. The subhousing 136 provides an enclosure for a battery compartment 151. The batteries 154 may be arranged on a base 155 in a circuit for providing heat through electrical resistance in the printed circuit board 139. The circuit board 139 may be designed to have multiple and separate heater sections built in to the circuit. The circuit may be rigid or flexible. The device is provided with an electronic control circuit to maintain printed circuit board (PCB) temperature of the heating circuit for warming the cleaning fluid. The heater is designed with enough resistance to allow heating, but to still protect against thermal runaway in a fault condition. The system may be provided with light emitting diodes or LED's to illuminate the separate ports for cleaning and white balance. The system may be provided with an on-off switch or there may simply be an insulating pull tab 157 that can be removed to complete the circuit. As shown in FIG. 9, two compartments are formed above the printed circuit board 139. The cleaning fluid 34 (FIG. 10) is warmed by the printed circuit board 139 and the warmed cleaning fluid 34 may be absorbed into the first and second cleaning materials 142 and 145. Accordingly, when a scope 115 is inserted into the first opening 106, the scope 115 can be pushed into contact with the cleaning material 142 to clean the end of the scope and to warm it for reinsertion into the cavity of the patient. When a scope 115 is inserted into the second opening 109, the scope 115 slides between the two sides 145a and 145b of the second cleaning material 145 such that a cleaning solution wipes off the scope 115 as it slides past. The scope 115 extends to the V-shaped white balance reference material 133 where it may be inserted until it makes contact. Because of the V-shape, the white balance reference material 133 is capable of accommodating scopes 115 having many different diameters.

Figure 11:
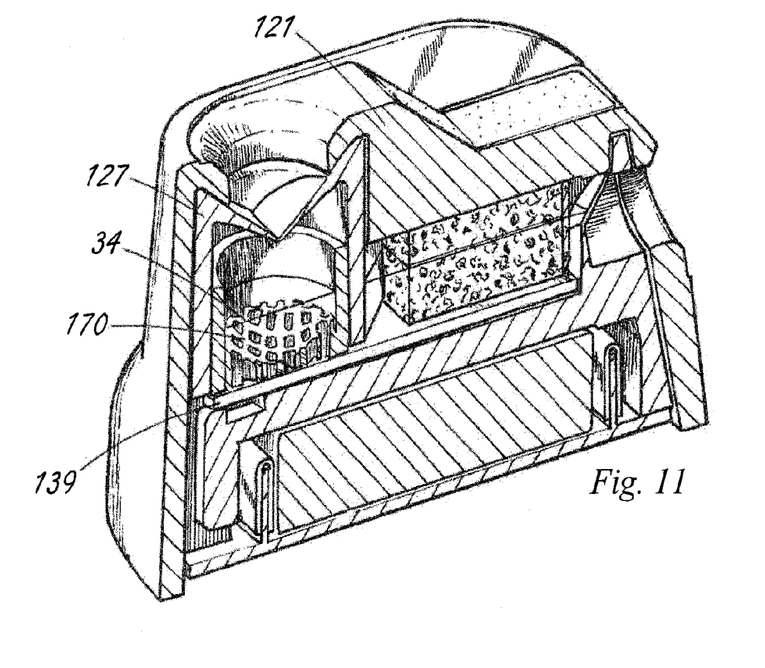
FIG. 11 is a detailed cross sectional view of an alternate embodiment of the scope cleaning device of FIG. 6.

Turning to FIG. 10, the cleaning fluid 34 may be contained in one or both of the chambers located above the printed circuit board 139. As shown, the fluid level may extend above the first cleaning material 142 and, if present in the second chamber 148, may extend for a majority of the height of the second cleaning material 145. The white balance reference material 133 is located above the fluid level as fluid on the white balance reference material 133 would disrupt the white balancing and would not produce good results for the imaging. As an alternative, the first and second chamber 124, 148 may be separate and the second chamber 148 may not contain fluid. The white balance reference material 133 is preferably a non-porous silicone material that does not absorb or retain any cleaning fluid solution. Turning to FIG. 11, the first cleaning material 142 may comprise a sponge or it may comprise a cross-hatched silicone cleaning material 170. The cross-hatched silicone material 170 may provide superior cleaning of the surface of the scope in comparison to a sponge. The use of a silicone or similar flexible material in a cross hatched pattern provides additional surface area for the cleaning material and provides improved cleaning of the lens.

Figure 12:
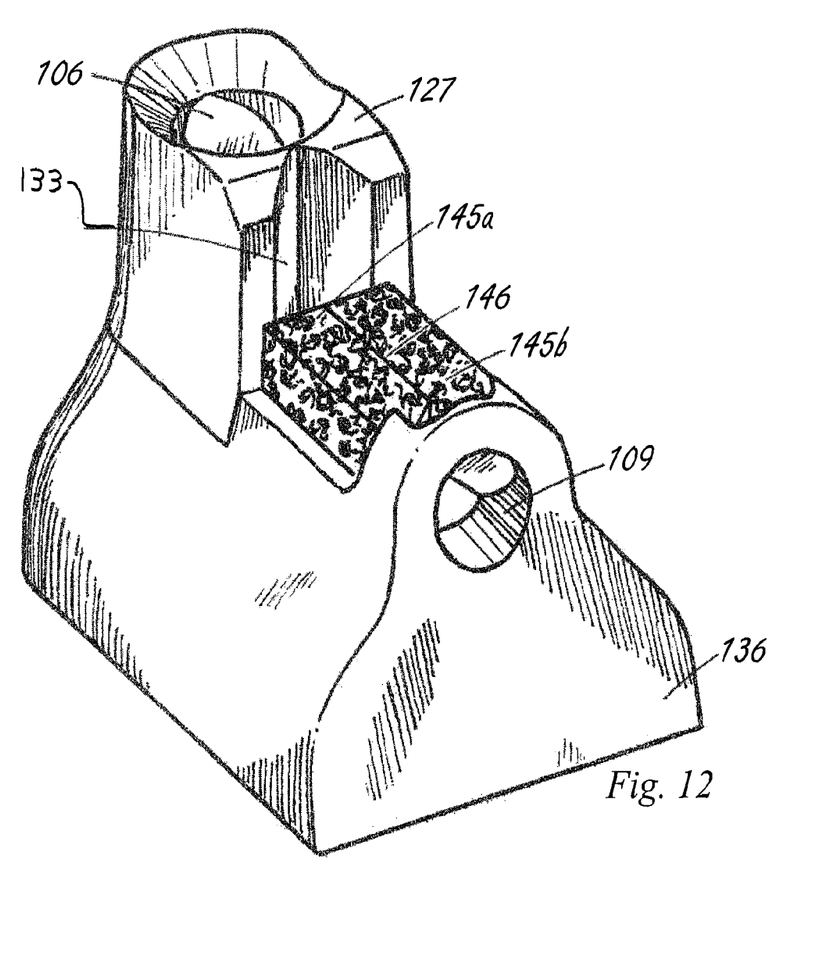
FIG. 12 is a perspective view of the portion of the scope cleaning device of FIG. 6 containing the white balance reference material.

In FIG. 12, the arrangement of the horizontal cavity is shown in greater detail. The second opening 109 extends to a chamber having a pair of sponges 145a and 145b with a longitudinal channel 146 disposed between the sponges. A white balance reference material 133 is disposed in spaced apart relation from the end of the sponges. The scope 115 may extend through the channel 146 between the sponges and may extending into contact with the white balance reference material 133 for white balancing according to the specifications for the camera. As shown in FIG. 13, the stand 46 may be disposed in spaced apart relation to the scope cleaning device 100 so that the scope 115 may be supported in a substantially horizontal configuration.

Figure 14A:
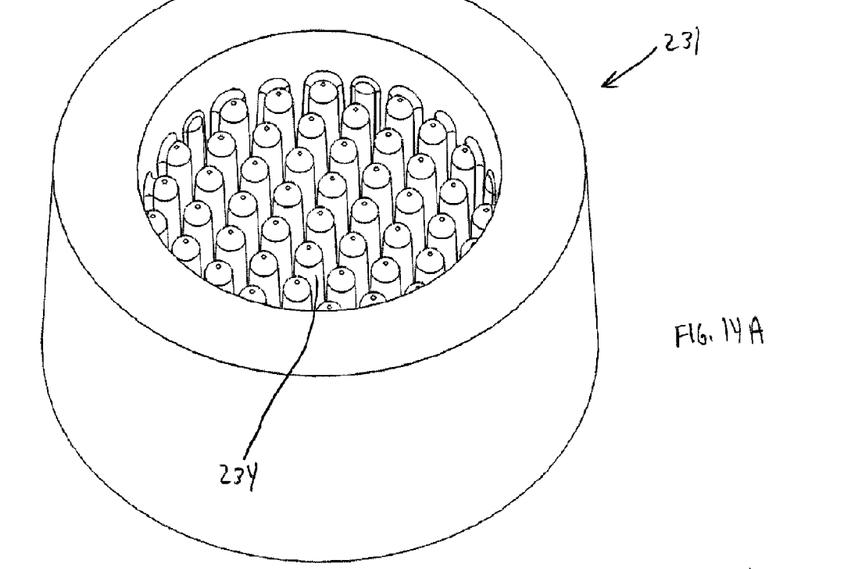
FIG. 14A is a perspective view of an alternate embodiment of the cleaning material.
Figure 14B:
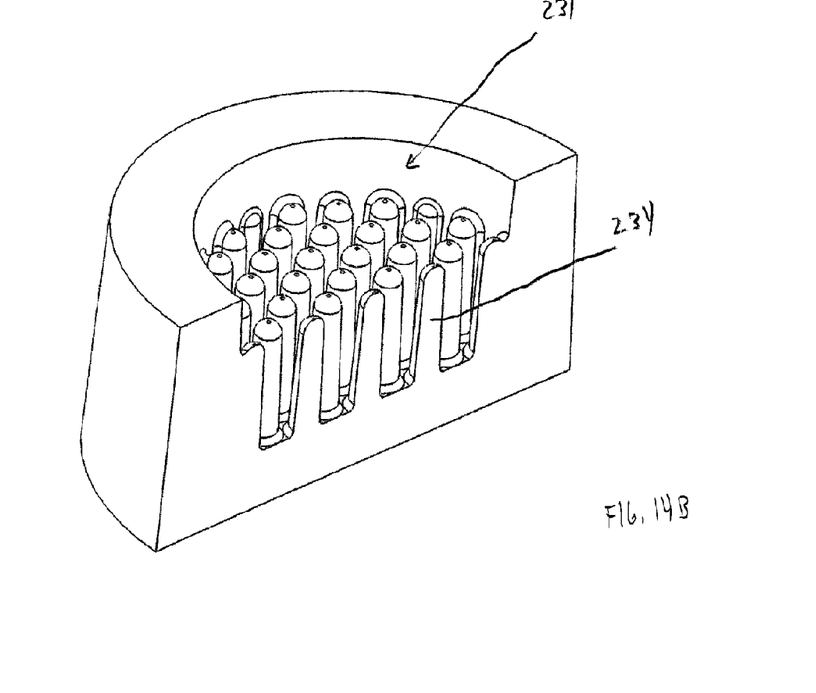
FIG. 14B is a cross-sectional perspective view of the embodiment shown in FIG. 14A.

Turning to FIGS. 14A-14B, an alternate embodiment of the cleaning material 31 in the first cavity 28 is shown. Cleaning material 231 includes a plurality of upstanding finger-like projections 234. The finger-like projections 234 provide a surface for cleaning a surgical scope inside the cavity 28.

Figures 15A, 15B:
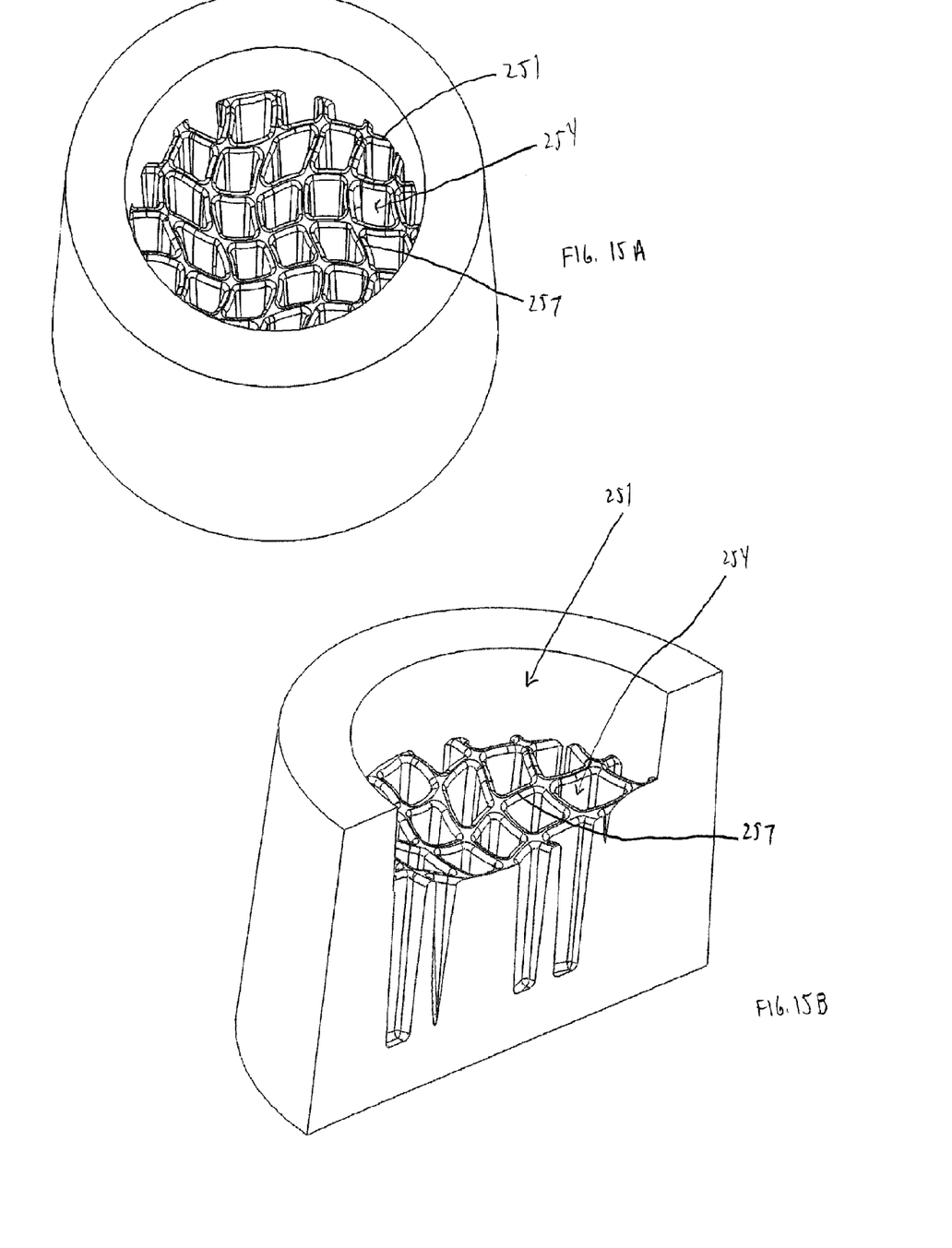
FIG. 15A is a perspective view of another alternate embodiment of the cleaning material.
FIG. 15B is a cross-sectional perspective view of the embodiment shown in FIG. 15A.

In FIG. 15A-15B, an another alternate embodiment of the cleaning material 31 is shown. A honey-comb like structure 251 includes a plurality of openings 254 divided by connecting walls 257.

Figure 16:
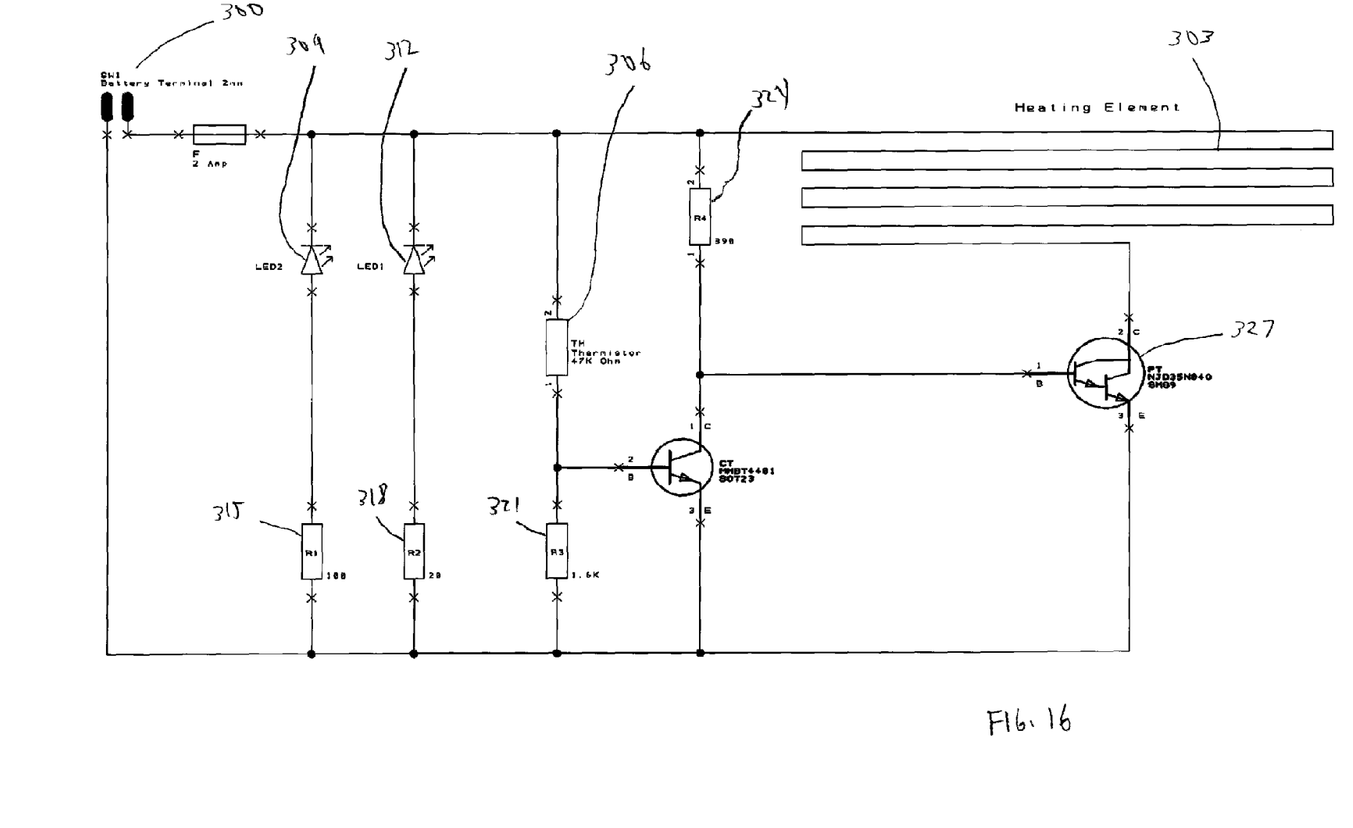
FIG. 16 is a schematic diagram of the electrical circuit of the present invention.

FIG. 16 is a schematic diagram of one embodiment of the electrical circuit. The circuit 299 includes a power source such as a battery 300; a heating element 303; a thermistor 306; a plurality of LED's 309, 312; and a plurality of resistors 315, 318, 321, and 324. The circuit components may be integrated into a single printed circuit board. With the heater and components integrated into one board, any heat generated by the power transistor 327 which controls the power going to the heating element 303 is also used to warm the fluid. Also, with the temperature sensor (thermistor 306) integrated into the same board that includes the heating element, there is little to no latency in sensing temperature changes. In the case of a battery powered circuit, the circuit may electronically adjust for the varying voltage over the battery life with pulse width modulation. This feature may be used to maintain the required temperature setpoint of the device over the expected range of four to six hours.

The present invention contemplates that many changes and modifications may be made. Therefore, while the presently-preferred form of the emissions measuring system has been shown and described, and several modifications and alternatives discussed, persons skilled in this art will readily appreciate that various additional changes and modifications may be made without departing from the spirit of the invention, as defined and differentiated by the following claims.

What is claimed is:

1. A cleaning and defogging device for use with a surgical scope during medical procedures, the device comprising:
   a housing defining a first cavity and a second cavity, the first cavity configured and arranged to receive a surgical scope in a generally vertical orientation, the second cavity configured and arranged to receive a surgical scope in a generally horizontal configuration, the housing having a first inlet communicating with the first cavity to allow a distal end of the surgical scope to be inserted into the first cavity through the first inlet, the housing having a second inlet communicating with the second cavity to allow a distal end of the surgical scope to be inserted into the second cavity through the second inlet;
   a cleaning fluid disposed in the first cavity;
   a heating element disposed in the housing such that heat is transferred from the heating element to the cleaning fluid;
   a V-shaped surface configured and arranged to receive a white balance referencing material, the V-shaped surface disposed inside the housing adjacent to the second cavity; and
   a power source configured and arranged to energize the heating element to produce heat for heating the cleaning fluid.

2. The device of claim 1, further comprising a cleaning material disposed in the first cavity.

3. The device of claim 2, wherein the cleaning material comprises a sponge.

4. The device of claim 2, wherein the cleaning material comprises a flexible material having a cross-hatched pattern.

5. The device of claim 2, wherein the cleaning material comprises a plurality of upstanding finger-like projections.

6. The device of claim 2, wherein the cleaning material comprises a material having a honeycomb-like structure.

7. The device of claim 1, wherein the first cavity and the second cavity are disposed in fluid communication.

8. The device of claim 7, wherein the cleaning fluid is disposed in the first and second cavity and is capable of moving therebetween.

9. The device of claim 1, further comprising an illumination source disposed adjacent to at least one of the first and second inlets.

10. The device of claim 1, further comprising a stand disposed in spaced apart relation to the second inlet, the stand configured and arranged to support the proximal end of the surgical scope when the distal end of the surgical scope is disposed in the second cavity.

11. The device of claim 1, further comprising a first subhousing having an upper surface and having a first subhousing cavity defined therein.

12. The device of claim 11, wherein the upper surface of the subhousing is configured and arranged to support a circuit board having a heating element disposed thereon.

13. The device of claim 12, further comprising a power source disposed inside the subhousing cavity.

14. The device of claim 13, wherein the power source comprises a plurality of batteries.

15. The device of claim 12, further comprising a second subhousing having a chamber forming the first cavity and having a V-shaped exterior surface for receiving the white balance reference material.

16. The device of claim 1, further comprising a second cleaning material disposed in the second cavity, the second cleaning material having a first portion and a second portion disposed in spaced apart relation such that a gap is formed between the first and second portions, the surgical scope being received in the gap and making contact with the first and second portions when the surgical scope is inserted into the second cavity through the second inlet.

17. The device of claim 1, wherein the heating element is a resistance type electrical heating element incorporated into an electrical circuit.

18. The device of claim 17, wherein the electrical circuit comprises a printed circuit board.

19. The device of claim 17, wherein the circuit comprises a thermistor for controlling the temperature of the cleaning solution within the housing.

20. The device of claim 17, wherein the circuit electronically adjusts for varying voltage over the life of a battery by pulse width modification.

21. The device of claim 19, wherein the thermistor and the heating element are incorporated into a single printed circuit board.

22. A cleaning and defogging device for use with a surgical scope during medical procedures, the device comprising:
a housing defining a first cavity and a second cavity, the first cavity configured and arranged to receive a surgical scope in a generally vertical orientation, the second cavity configured and arranged to receive a surgical scope in a generally horizontal configuration, the first cavity and second cavity disposed in fluid communication, the housing having a first inlet communicating with the first cavity to allow a distal end of the surgical scope to be inserted into the first cavity through the first inlet, the housing having a second inlet communicating with the second cavity to allow a distal end of the surgical scope to be inserted into the second cavity through the second inlet;
a cleaning fluid disposed in the first cavity and second cavity and capable of moving therebetween;
a heating element disposed in the housing such that heat is transferred from the heating element to the cleaning fluid;
a power source configured and arranged to energize the heating element to produce heat for heating the cleaning fluid; and,
wherein a white balance reference material is disposed in the second cavity above the level of the cleaning fluid.

23. A cleaning and defogging device for use with a surgical scope during medical procedures, the device comprising:
a housing defining a first cavity and a second cavity, the first cavity configured and arranged to receive a surgical scope in a generally vertical orientation, the second cavity configured and arranged to receive a surgical scope in a generally horizontal configuration, the first cavity and second cavity disposed in fluid communication, the housing having a first inlet communicating with the first cavity to allow a distal end of the surgical scope to be inserted into the first cavity through the first inlet, the housing having a second inlet communicating with the second cavity to allow a distal end of the surgical scope to be inserted into the second cavity through the second inlet;
a first cleaning material disposed in the first cavity;
a white balance reference material disposed in the housing and configured and arranged to white balance a surgical scope disposed in the housing;
a cleaning fluid disposed in the first cavity;
an electrical circuit having a heating element operatively associated therewith, the heating element disposed in the housing such that heat is transferred from the heating element to the cleaning fluid;
a power source configured and arranged to energize the heating element to produce heat for heating the cleaning fluid;
wherein the housing has a first subhousing and a second subhousing disposed therein, the first subhousing having an upper surface and having a first subhousing cavity defined therein, the heating element disposed on the upper surface, the power source disposed in the first subhousing cavity, the second subhousing forming the first cavity and having a V-shaped exterior surface configured and arranged to receive the white balancing reference material.

24. The device of claim 23, wherein the upper surface of the first subhousing is disposed underneath the first cavity in the housing to warm the cleaning fluid.

25. The device of claim 23, wherein the electrical circuit comprises a printed circuit board.

* * * * *